United States Patent
Chopra et al.

(10) Patent No.: US 9,918,659 B2
(45) Date of Patent: Mar. 20, 2018

(54) SHAPE SENSOR SYSTEMS FOR TRACKING INTERVENTIONAL INSTRUMENTS AND MEHODS OF USE

(71) Applicant: Intuitive Surgical Operations, Inc., Sunnyvale, CA (US)

(72) Inventors: Prashant Chopra, Sunnyvale, CA (US); Vincent Duindam, Mountain View, CA (US); Tao Zhao, Sunnyvale, CA (US); John A Cole, Hollister, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 236 days.

(21) Appl. No.: 14/204,807

(22) Filed: Mar. 11, 2014

(65) Prior Publication Data

US 2014/0275997 A1    Sep. 18, 2014

Related U.S. Application Data

(60) Provisional application No. 61/799,524, filed on Mar. 15, 2013.

(51) Int. Cl.
| | |
|---|---|
| *A61B 5/05* | (2006.01) |
| *A61B 5/06* | (2006.01) |
| *A61B 5/00* | (2006.01) |
| *A61B 34/20* | (2016.01) |
| *A61B 34/30* | (2016.01) |
| *A61B 34/10* | (2016.01) |
| *A61B 90/00* | (2016.01) |

(52) U.S. Cl.
CPC .............. *A61B 5/064* (2013.01); *A61B 34/20* (2016.02); *A61B 34/30* (2016.02); *A61B 5/6879* (2013.01); *A61B 2034/105* (2016.02); *A61B 2034/2061* (2016.02); *A61B 2034/301* (2016.02); *A61B 2034/303* (2016.02); *A61B 2090/363* (2016.02); *A61B 2090/3937* (2016.02); *A61B 2090/3966* (2016.02); *A61B 2560/0456* (2013.01)

(58) Field of Classification Search
USPC ........................................................ 600/424
See application file for complete search history.

(56) References Cited

U.S. PATENT DOCUMENTS

| | | |
|---|---|---|
| 6,380,732 B1 | 4/2002 | Gilboa |
| 6,381,485 B1 | 4/2002 | Hunter et al. |
| 6,389,187 B1 | 5/2002 | Greenaway et al. |

(Continued)

FOREIGN PATENT DOCUMENTS

| | | |
|---|---|---|
| EP | 2436333 A1 | 4/2012 |
| WO | WO-0133165 A1 | 5/2001 |

OTHER PUBLICATIONS

International Search Report and Written Opinion for Application No. PCT/US14/23450, dated Jul. 17, 2014, 15 pages.

(Continued)

*Primary Examiner* — Joel F Brutus

(57) ABSTRACT

A medical tracking system comprises a fiducial apparatus that includes a sensor docking feature configured to mate with a mating portion of a sensor device. The sensor docking feature retains the mating portion in a known configuration. The fiducial apparatus also includes at least one imageable fiducial marker and a surface configured for attachment to an anatomy of a patient.

38 Claims, 9 Drawing Sheets

(56) References Cited

U.S. PATENT DOCUMENTS

| | | | |
|---|---|---|---|
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,241,274 B2 | 8/2012 | Keogh et al. | |
| 2002/0087101 A1* | 7/2002 | Barrick | A61B 5/1077 600/587 |
| 2002/0183592 A1* | 12/2002 | Suzuki | A61B 1/00071 600/145 |
| 2004/0030236 A1* | 2/2004 | Mazzocchi | A61B 34/20 600/414 |
| 2006/0013523 A1 | 1/2006 | Childers et al. | |
| 2006/0184016 A1 | 8/2006 | Glossop | |
| 2009/0137952 A1* | 5/2009 | Ramamurthy | A61B 5/06 604/95.01 |
| 2009/0314925 A1* | 12/2009 | Van Vorhis | A61B 19/5244 250/203.2 |
| 2010/0149183 A1* | 6/2010 | Loewke | G06K 9/00134 345/424 |
| 2010/0168562 A1 | 7/2010 | Zhao et al. | |
| 2010/0202727 A1* | 8/2010 | Prisco | A61B 19/2203 385/13 |
| 2011/0113852 A1* | 5/2011 | Prisco | G01B 11/18 73/1.15 |
| 2012/0289777 A1 | 11/2012 | Chopra et al. | |
| 2013/0028554 A1 | 1/2013 | Wong et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages Extended European Search Report for Application No. 14769738.7, dated Sep. 20, 2016, 8 pages.

* cited by examiner

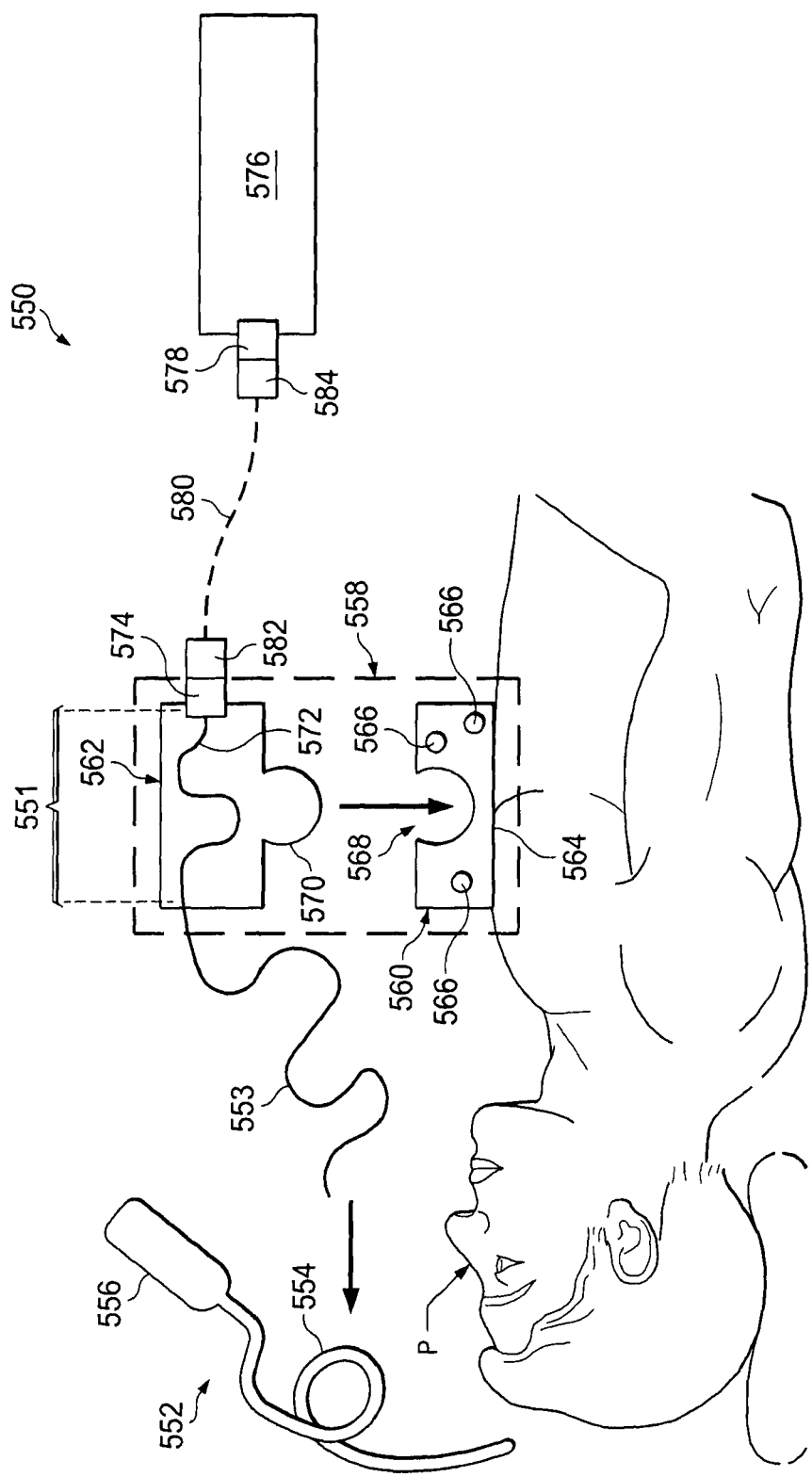

SHAPE SENSOR SYSTEMS FOR TRACKING INTERVENTIONAL INSTRUMENTS AND MEHODS OF USE

CROSS-REFERENCE TO RELATED APPLICATIONS

This application claims the benefit of U.S. Provisional Application 61/799,524 filed Mar. 15, 2013, which is incorporated by reference herein in its entirety.

FIELD

The present disclosure is directed to systems and methods for navigating a patient anatomy to conduct a minimally invasive procedure, and more particularly to systems and methods using shape sensor systems to track interventional instruments.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. In existing systems, electromagnetic (EM) navigation may be used to track the movement of interventional instruments through a patient anatomy. Although EM navigation systems are useful for many procedures, they may be subject to magnetic interference from other equipment in the surgical suite. For example, a C-arm of a fluoroscopic imaging system or metal instruments may generate magnetic interference with EM navigation systems, causing unacceptable errors in the tracking of an interventional instrument. Improved navigation systems and methods are needed for tracking interventional instruments in surgical environments, including in environments where EM navigation is not suitable or may be compromised.

SUMMARY

The embodiments of the invention are summarized by the claims that follow the description.

In one embodiment, a medical tracking system comprises a fiducial apparatus that includes a sensor docking feature configured to mate with a mating portion of a sensor device. The sensor docking feature retains the mating portion in a known configuration. The fiducial apparatus also includes at least one imageable fiducial marker and a surface configured for attachment to an anatomy of a patient.

In another embodiment, a method for medical instrument tracking comprises receiving a model of an anatomic structure. The model defines an image reference frame and includes an image of at least one fiducial marker. The method further includes registering a reference portion of a first shape sensor device to the plurality of fiducial markers when a fiducial apparatus, including the at least one fiducial marker, is coupled to the first shape sensor device. The reference portion of the first shape sensor device is retained in a known configuration relative to the at least one fiducial marker. The method further comprises receiving first shape sensor information in a first sensor reference frame from a first shape sensor of the first shape sensor device and determining a pose of the first shape sensor in the image reference frame based on a correlation between the image reference frame and the first sensor reference frame.

A method for medical instrument tracking comprises receiving a model of an anatomic structure. The model defining an image reference frame and including a model of at least one fiducial marker. The method further includes receiving first shape sensor information in a first reference frame from a first shape sensor including a reference portion held in a known configuration with respect to the at least one fiducial marker. The method further includes receiving second shape sensor information in a second reference frame from a second shape sensor positioned within the anatomic structure. The method further includes determining a pose of the second shape sensor in the image reference frame based on a correlation between the first reference frame, the second reference frame, and the image reference frame.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 10 illustrates an interventional instrument system with a tracking system according to other embodiments of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
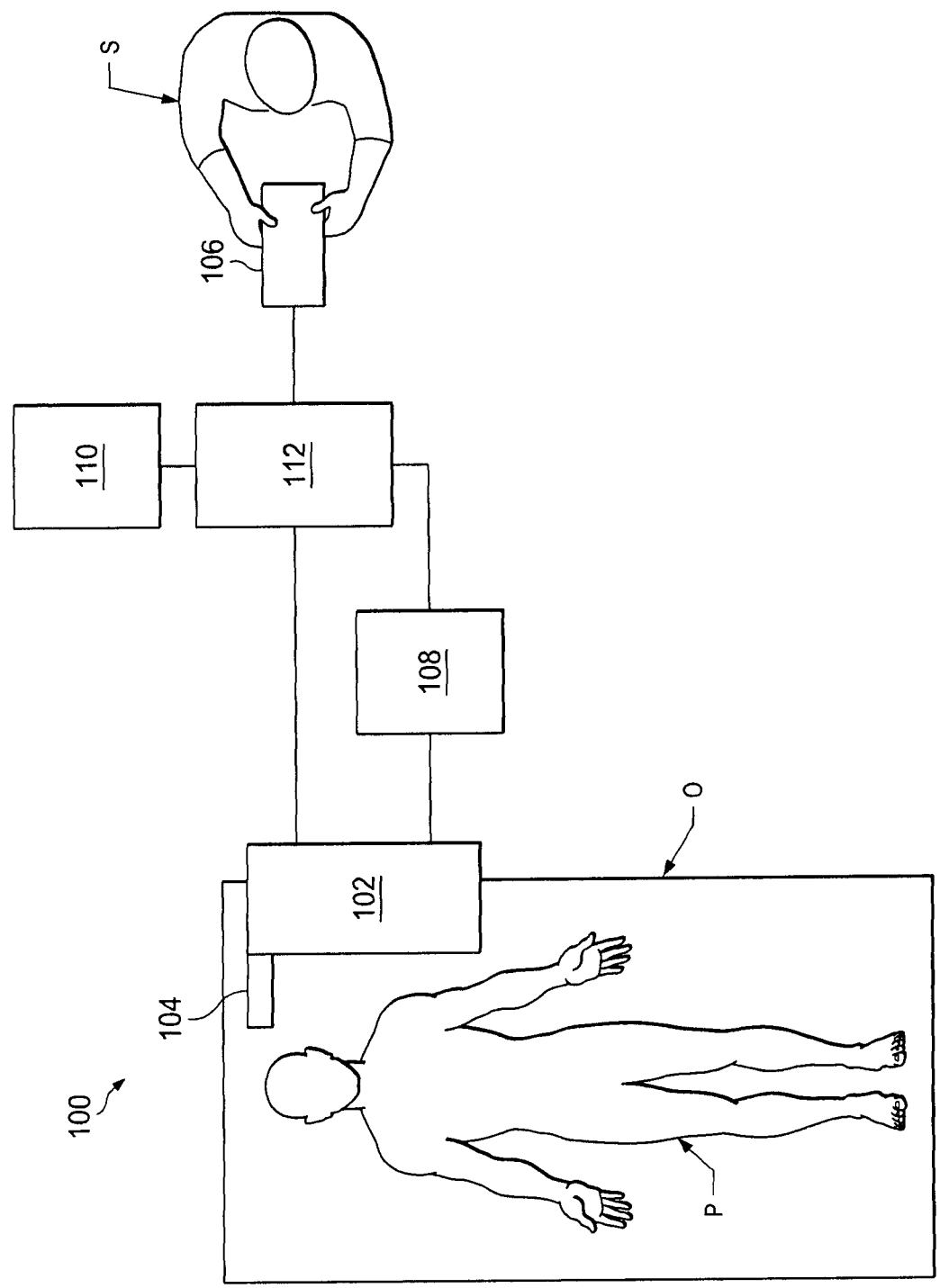
FIG. 1 is a robotic interventional system, in accordance with an embodiment of the present disclosure.

Referring to FIG. 1 of the drawings, a robotic interventional system for use in, for example, surgical, diagnostic, therapeutic, or biopsy procedures, is generally indicated by the reference numeral 100. As shown in FIG. 1, the robotic interventional system 100 generally includes a robotic assembly 102 mounted to or near an operating table O on which a patient P is positioned. An interventional instrument system 104 is operably coupled to the robotic assembly 102. An operator input system 106 allows a surgeon or clinician S to view the surgical site and to control the operation of the interventional instrument system 104.

The operator input system 106 may be located at a clinician's console which is usually located in the same room as operating table O. However, it should be understood that the surgeon or clinician S can be located in a different room or a completely different building from the patient P. Operator input system 106 generally includes one or more control device(s) for controlling the interventional instrument system 104. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the clinician with telepresence, or the perception that the control device(s) are integral with the instruments so that the clinician has a strong sense of directly controlling instruments. In other embodiments, the control device(s) may have more or fewer degrees of freedom than the associated interventional instruments and still provide the clinician with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 102 supports the interventional instrument system 104 and may comprise a kinematic structure of one or more non-servo controlled links (e.g., one or more links that may be manually positioned and locked in place, generally referred to as a set-up structure) and a robotic manipulator. The robotic assembly 102 includes plurality of actuators (e.g., motors) that drive inputs on the interventional instrument 104. These motors actively move in response to commands from the control system (e.g., control system 112). The motors include drive systems which when coupled to the interventional instrument 104 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 100 also includes a sensor system 108 with one or more sub-systems for receiving information about the instruments of the robotic assembly. Such sub-systems may include a position sensor system (e.g., an electromagnetic (EM) sensor system); a shape sensor system for determining the position, orientation, speed, pose, and/or shape of the catheter tip and/or of one or more segments along a flexible body of instrument 104; and/or a visualization system for capturing images from the distal end of the catheter system.

The robotic interventional system 100 also includes a display system 110 for displaying an image of the surgical site and interventional instruments 104 generated by sub-systems of the sensor system 108. The display 110 and the operator input system 106 may be oriented so the operator can control the interventional instrument system 104 and the operator input system 106 as if viewing the workspace in substantially true presence. True presence means that the displayed tissue image appears to an operator as if the operator was physically present at the image location and directly viewing the tissue from the perspective of the image.

Alternatively or additionally, display system 110 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images and models.

In some embodiments, the display system 110 may display a virtual visualization image in which the actual location of the interventional instrument is registered (e.g., dynamically referenced) with preoperative or concurrent images to present the clinician with a virtual image of the internal surgical site at the location of the tip of the surgical instrument.

In other embodiments, the display system 110 may display a virtual visualization image in which the actual location of the interventional instrument is registered with prior images (including preoperatively recorded images) or concurrent images to present the clinician with a virtual image of an interventional instrument at the surgical site. An image of a portion of the interventional instrument 104 may be superimposed on the virtual image to assist the clinician controlling the interventional instrument.

The robotic interventional system 100 also includes a control system 112. The control system 112 includes at least one processor (not shown), and typically a plurality of processors, for effecting control between the interventional instrument system 104, the operator input system 106, the sensor system 108, and the display system 110. The control system 112 also includes programmed instructions (e.g., a computer-readable medium storing the instructions) to implement some or all of the methods described herein. While control system 112 is shown as a single block in the simplified schematic of FIG. 1, the system may comprise a number of data processing circuits with a portion of the processing optionally being performed on or adjacent the robotic assembly 102, a portion being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers to provide force and torque feedback from the interventional instrument system 104 to one or more corresponding servomotors for the operator input system 106. The servo controller(s) may also transmit signals instructing robotic assembly 102 to move the interventional instruments 104 which extend into an internal surgical site within the patient body via openings in the body. Any suitable conventional or specialized servo controller may be used. A servo controller may be separate from, or integrated with, robotic assembly 102. In some embodiments, the servo controller and robotic assembly are provided as part of a robotic arm cart positioned adjacent to the patient's body.

The control system 112 may further include a virtual visualization system to provide navigation assistance to the interventional instruments 104. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung) or during induced anatomic motion (e.g., patient repositioning or instrument-caused deformation).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 100 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
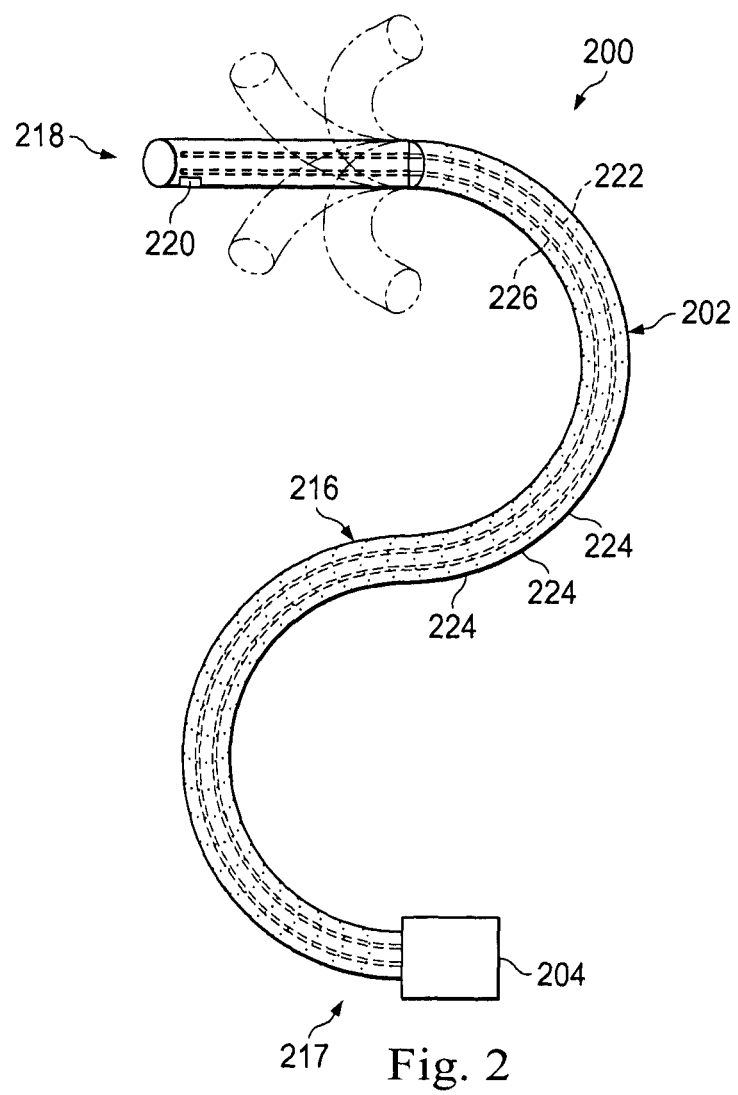
FIG. 2 illustrates an interventional instrument system utilizing aspects of the present disclosure.

FIG. 2 illustrates an interventional instrument system 200 which may be used as the interventional instrument system 104 of robotic interventional system 100. Alternatively, the interventional instrument system 200 may be used for non-robotic exploratory procedures or in procedures involving traditional manually operated interventional instruments, such as endoscopy.

The instrument system 200 includes a catheter system 202 coupled to an instrument body 204. The catheter system 202 includes an elongated flexible catheter body 216 having a proximal end 217 and a distal end 218. In one embodiment, the flexible body 216 has an approximately 3 mm outer diameter. Other flexible body outer diameters may be larger or smaller. The catheter system 202 includes a shape sensor 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. If the instrument system 200 is an interventional instrument system 104 of a robotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data. See e.g., FIG. 3.

The shape sensor system 222 includes an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed to detect the shape of the instrument system 202 and for utilizing that information to assist in surgical procedures. The sensor system (e.g. sensor system 108 or another typed of tracking system as described in FIG. 3) may include an interrogation system for generating and detecting the light used for determining the shape of the interventional instrument system 202. This information, in turn, in can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The interventional instrument system may optionally include a position sensor system 220 (e.g., an electromagnetic (EM) sensor system) which may be disabled by an operator or an automated system (e.g., a function of the control system 112) if it becomes unreliable due to, for example, magnetic interference from other equipment in the surgical suite or if other navigation tracking systems are more reliable.

The position sensor system 220 may be an EM sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 includes a channel sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like. In various embodiments, the auxiliary tool 226 may be an image capture probe including a tip portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The flexible catheter body 216 may also house cables, linkages, or other steering controls (not shown) that extend between the instrument body 204 and the distal end 218 to controllably bend or turn the distal end 218 as shown for example by the dotted line versions of the distal end. In embodiments in which the instrument system 200 is actuated by a robotic assembly, the instrument body 204 may include drive inputs that couple to motorized drive elements of the robotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. Also or alternatively, the flexible body 216 can define one or more lumens through which interventional instruments can be deployed and used at a target surgical location.

In various embodiments, the interventional instrument system 202 may be a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

Figure 3:
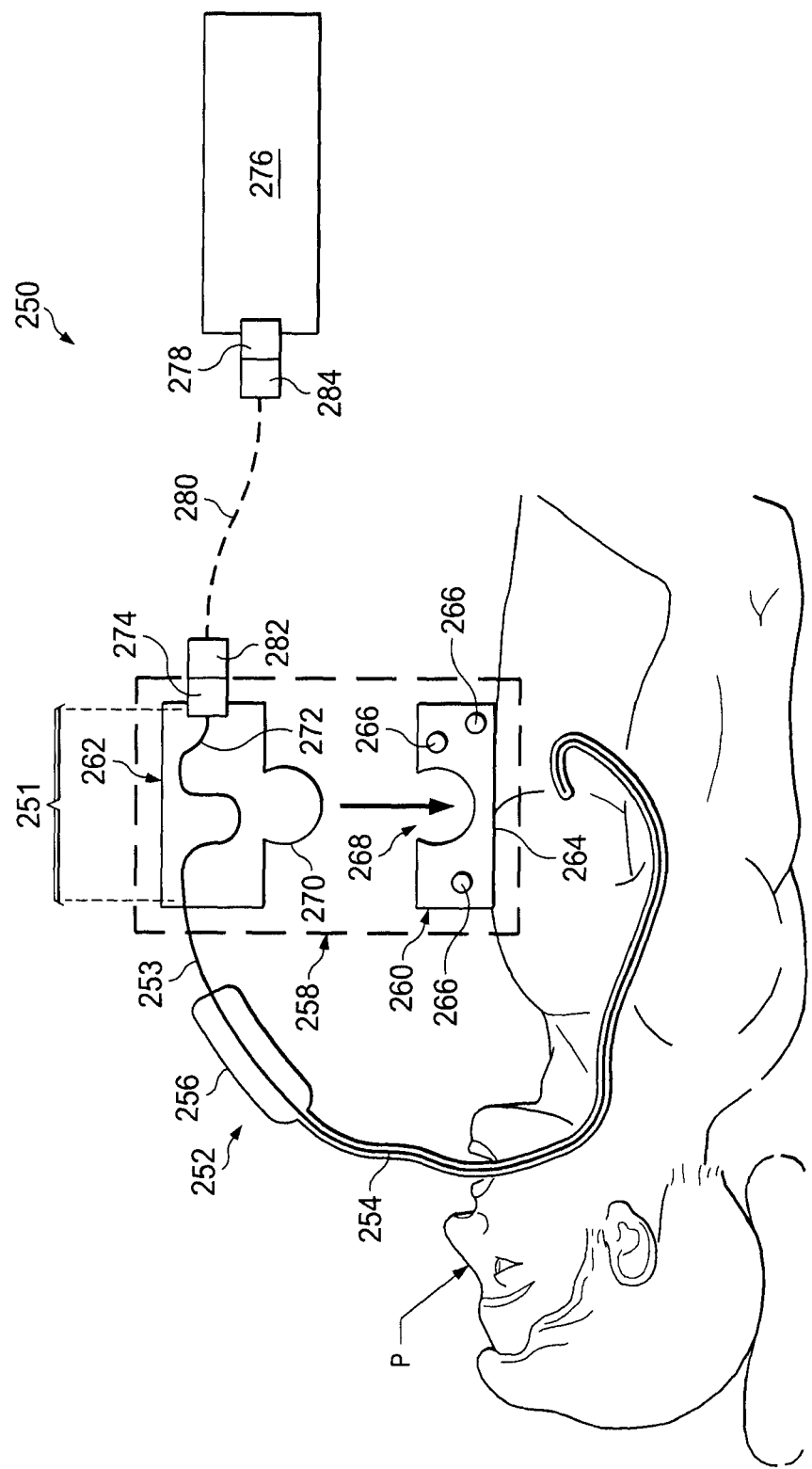
FIG. 3 illustrates an interventional instrument system with a tracking system according to an embodiment of the present disclosure.

FIG. 3 illustrates an interventional instrument tracking system 250 according to embodiments of the present disclosure. The tracking system 250 includes an interventional instrument 252 with a flexible catheter body 254 and an instrument body 256. The interventional instrument 252 may be similar to instrument 200 but in this embodiment, the EM position sensor may be disabled or omitted, as the shape sensing system provides the tracking information used by the clinician to determine the path of the interventional instrument through the patient anatomy. An optical fiber shape sensor 253 extends within the interventional instrument 252. The tracking system 250 also includes a sensor device 258. The sensor device 258 includes a fiduciary apparatus 260 and a reference body 262. The fiduciary apparatus 260 includes a surface 264 that is removably attached to the patient P using an adhesive or other chemical or mechanical fixation mechanism. In some embodiments, the fiduciary apparatus 260 is attached to an external surface of the patient anatomy, but in alternative embodiments, the fiduciary apparatus may be attached to the internal patient anatomy, e.g., trans-nasal, trans-rectal, trans-vaginal, trans-esophageal. In still other alternatives, the fiduciary apparatus 260 may be attached to a temporary implant such as a stent.

The fiduciary apparatus 260 can include at least one fiducial marking 266 visible with imaging technology such as fluoroscopy or CT. Examples of fiduciary marker design are provided in U.S. patent application Ser. No. 12/428,657, filed Apr. 23, 2009, disclosing "Fiducial Marker Design and Detection for Locating Surgical Instrument in Images," which is incorporated by reference herein in its entirety. The fiducial marking may have sufficient detail to provide full three dimensional pose registration. For example, the fiduciary marking may have an "L"-shape with uneven link lengths that allow for three-dimensional pose registration. In various other embodiments, the fiduciary apparatus 260 can include features (e.g., grooves, protrusions, or other shapes) that are visible under imaging technology and can act as fiducials. In various other embodiments, the fiduciary apparatus 260 itself can act as a fiducial, and in some embodiments may have a shape that facilitates three-dimensional pose determination.

The fiduciary apparatus 260 further includes a sensor docking feature 268 configured to mate with a mating portion 270 of the reference body 262. The sensor docking feature 268 may include one or more recesses, protrusions, mechanical fasteners, adhesive fasteners, magnetic fasteners, or other components for removably connecting the fiduciary apparatus 260 to the reference body 262. When connected, the sensor docking feature 268 and the mating portion 270 maintain the fiduciary apparatus 260 and the reference body 262 in a known predefined and fixed spatial relationship.

Figure 4:
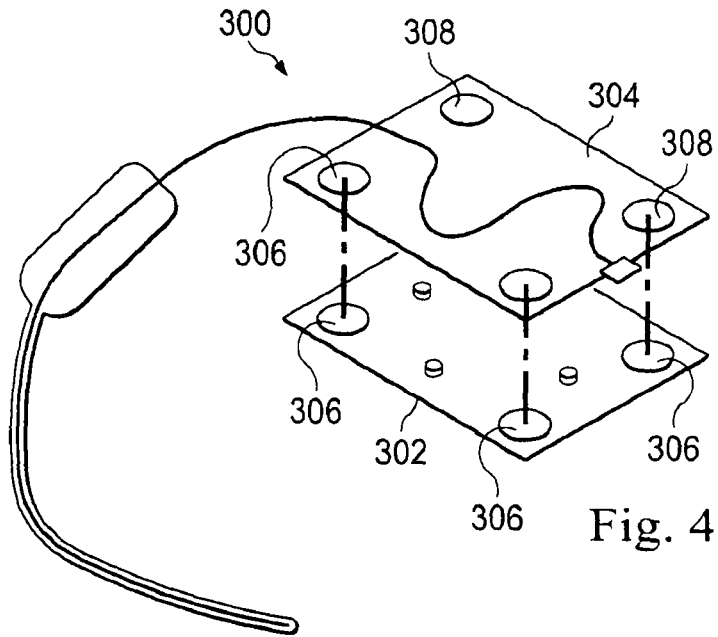
FIG. 4 illustrates a sensor device according to an embodiment of the present disclosure.

FIG. 4 illustrates an alternative embodiment of a sensor device 300 including a fiduciary apparatus 302 and a reference body 304. In this embodiment, a plurality of sensor docking features 306 of the fiduciary apparatus 302 align with and attach to mating portions 308 of the reference body 304.

Referring again to FIG. 3, the reference body 262 include a sensor holder 272 configured to hold a reference portion 251 the shape sensor fiber 253 in a predefined reference shape. In this embodiment, the sensor holder 272 is a continuous winding channel that receives the shape sensor fiber 253 and maintains the fiber in a predefined shape configuration relative to the reference body 262. In alternative embodiments, the sensor holder may be a series of discrete attachment points to which the sensor fiber may be attached to maintain a predefined shape with respect to the reference body. The reference body 262 further includes a sensor connection component 274 in which the sensor fiber 253 terminates for connection to other components of the tracking system 250.

The tracking system 250 further includes an interrogation system 276 for generating, and detecting the light used to determine the current shape of the shape sensor fiber 253. The interrogation system 276 may also process the returned data for display to the clinician. The interrogation system 276 includes a connector 278. A fiber link 280 extends between connectors 282, 284. In this embodiment, the optical fiber of the fiber link 280 is unsensed (i.e., the shape of the fiber link is not interrogated) and serves to convey the optical information from the sensed shape sensor 253 to the interrogation system 276. In use, the connector 282 of the fiber link 280 is connected to the connector 274 and the connector 284 is connected to the connector 278.

In use, the fiduciary apparatus 260 is attached to the patient P. Pre-operative or intra-operative imaging of the patient P is conducted with the fiduciary apparatus 260 attached. The fiducial markers 266 are visible in the image and thus provide a reference frame fixed relative to the anatomy of patient P and to any two-dimensional, three-dimensional, or four-dimensional (i.e., moving with time) models of the patient anatomy generated by the images (i.e., fiducial markers 266 define a set of reference points having a known relationship to at least a portion of the model data for the patient anatomy). In various other embodiments, reference body 260 can be coupled to the fiduciary apparatus during the pre-operative imaging of the patient P, such that optional fiducial markers, elements, or even the reference portion 251 if the shape sensor fiber 253 can be used as fiducials.

In any event, before initiating the interventional procedure, the reference body 262 is coupled to the fiduciary apparatus 260 and is held in a predefined configuration relative to the fiduciary apparatus by the docking feature 268 and the mating portion 270. Thus connected, the reference portion 251 of the shape sensor fiber 253 provides a known pose of the proximal end of the shape sensor fiber relative to the fiduciary apparatus 260. The interrogation system 276 interrogates the shape sensor fiber 253 to determine the pose of the distal tip and the shape of the flexible catheter body 254. This sensed relative pose and shape data for the catheter body 254 is known relative to the reference portion 251 of the shape sensor fiber, which is registered to the fiduciary apparatus 260. Thus, processing the relative pose and shape information for the catheter body 254 with the registration information for the reference portion 251 of the shape sensor fiber provides the pose and shape of the catheter body 254 relative to the patient P.

In various alternative embodiments to the above described fixed and predefined configuration of the reference body and fiduciary apparatus, the configuration of the reference body and the fiduciary apparatus may variable but with a measurable variation. This configuration is also known but is measurable instead of predefined. For example, the fiduciary apparatus and the reference body may be spaced apart by a small variable distance but the small distance may be continuously monitored and recorded by a sensor-based variation tracking system including capacitive sensors, piezo-electric sensors, or optical sensors. As another example, the measurable variability may be an insertion direction distance which may be measured, for example using a motor encoder.

Figure 5:
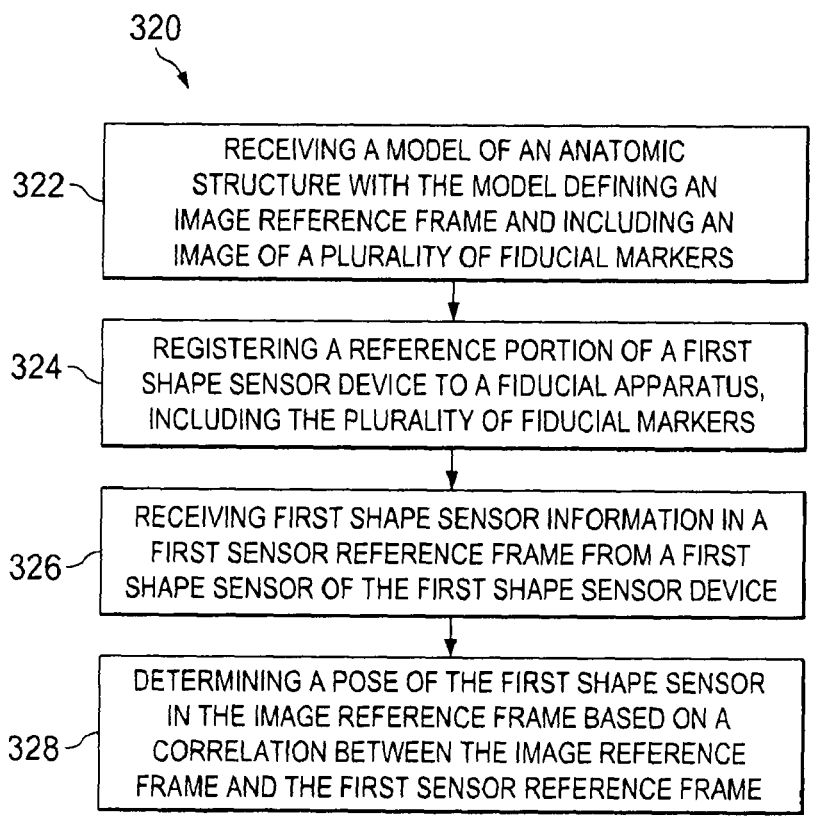
FIG. 5 illustrates a method of use for an interventional instrument tracking system according to an embodiment of the present disclosure.

FIG. 5 illustrates a method 320 for using the interventional instrument tracking system 250. At 322, a processing system receives a model of an anatomic structure of patient P. The model is generated from images of the patient P taken with the fiduciary apparatus 260 attached. The model defines an image reference frame. The fiducial markings 266 are visible in the model. At 324, the fiducial apparatus 260 is coupled to the reference body 262. The reference portion 251 of the shape sensor fiber 253 is thus retained in a predefined configuration relative to the fiducial apparatus 260. In this way, the reference portion 251 is registered to the fiduciary apparatus 260. At 326, the shape sensor information is received (in the reference frame of the shape sensor fiber 253) for processing. At 328, the pose of the distal end (or any other portion) of the shape sensor fiber 253 is determined in the image reference frame based on a registration between the image reference frame and the reference frame of the shape sensor 253. Optionally, an image from the image reference frame that corresponds to the pose of the distal end of the flexible body 254 is displayed. The image may be of the distal end of the flexible body 254 superimposed on an image from the patient model. In some embodiments, the patient model may be updated based on the shape sensor information (e.g., by fitting the patient model to the pose of flexible body 254). Alternatively, the image may be a view from inside the patient model corresponding to the view from the distal end of the flexible body.

Figure 6:
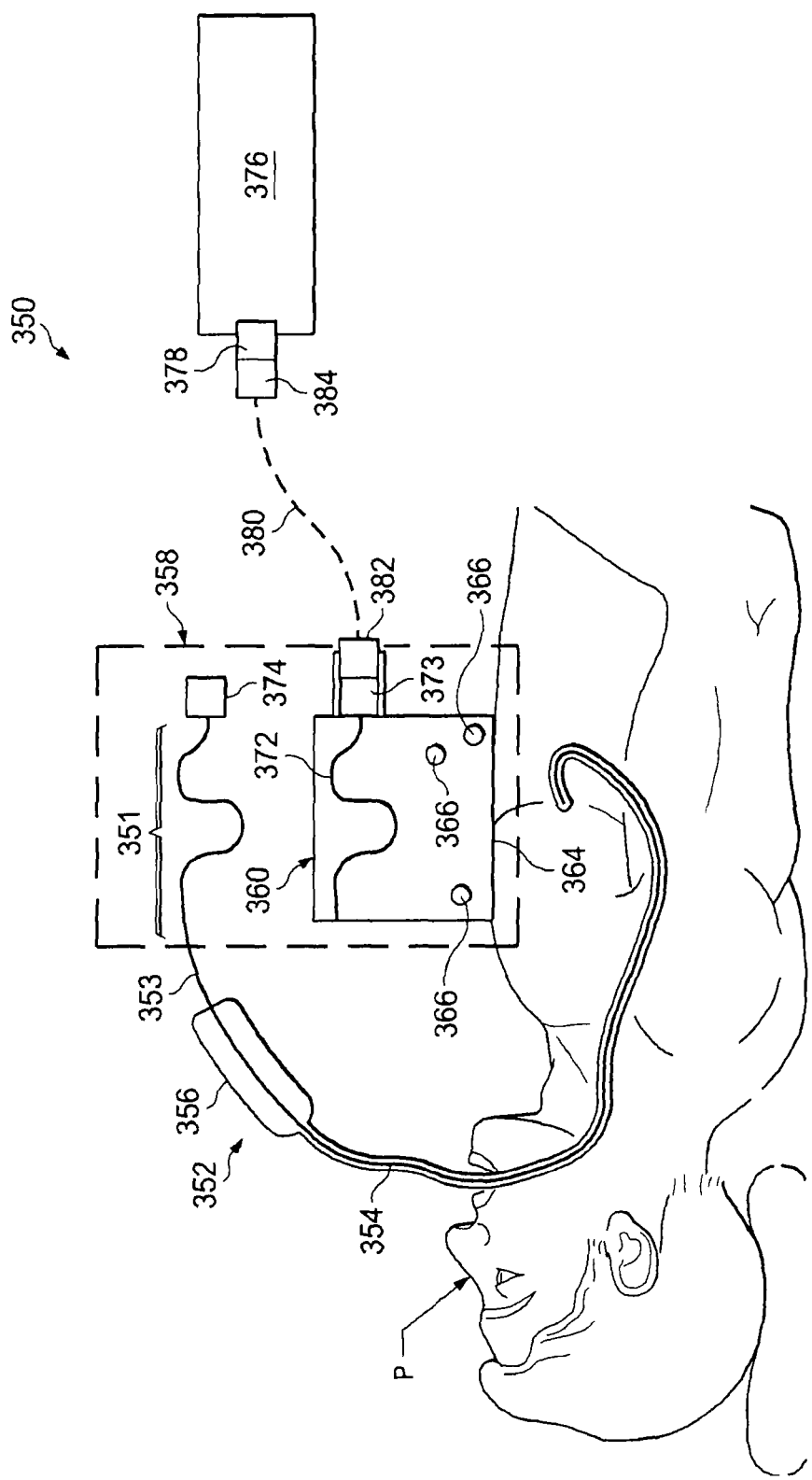
FIG. 6 illustrates an interventional instrument system with a tracking system according to another embodiment of the present disclosure.

FIG. 6 illustrates an interventional instrument tracking system 350 according to embodiments of the present disclosure. The tracking system 350 includes an interventional instrument 352 with a flexible catheter body 354 and an instrument body 356. An optical fiber shape sensor 353 extends within the interventional instrument 352. The tracking system 350 also includes a sensor device 358. The sensor device 358 includes a fiduciary apparatus 360 with a surface 364 that is removably attached to the patient P using an adhesive or other chemical or mechanical fixation mechanism. In various embodiments, the fiduciary apparatus 360 includes at least one fiducial marking 366 visible with imaging technology such as fluoroscopy or CT. In various other embodiments, the fiduciary apparatus 360 can include features, that can physical features that can be used as fiducials, or can even itself be a fiducial. The fiduciary apparatus 360 also includes a docking feature 373 for mating with a connector 374 of the shape sensor 353.

The fiduciary apparatus 360 includes a sensor holder 372 configured to dock a reference portion 351 of the shape sensor fiber 353, holding the portion 351 in a predefined reference shape. In this embodiment, the sensor holder 372 is a continuous winding channel that receives the reference portion 351 of the shape sensor fiber 253 and maintains the fiber in a known predefined shape configuration relative to the fiduciary apparatus 360. A sensor connection component 274 terminates the sensor fiber 353 and is removably connectable to the mating docking feature 373. In various alternative embodiments, the known configuration may be measurably variable as previously described.

The tracking system 350 further includes an interrogation system 376 for generating, and detecting the light used to determine the current shape of the shape sensor fiber 353. The interrogation system 376 may also process the returned data for display to the clinician. The interrogation system 376 includes a connector 378. A fiber link 380 extends between connectors 382, 384. In this embodiment, the optical fiber of the fiber link 380 is unsensed (i.e., the shape of the fiber link is not interrogated) and serves to convey the optical information from the sensed shape sensor 353 to the interrogation system 376. In use, the connector 382 of the fiber link 380 is connected to the connector 374 and the connector 384 is connected to the connector 378. In this embodiment the connectors 374, 382 are connected within a portion of the fiduciary apparatus 360.

In use, the fiduciary apparatus 360 is attached to the patient P. Pre-operative or intra-operative imaging of the patient P is conducted with the fiduciary apparatus 360 attached. If present, the fiducial markers 366 are visible in the image and thus provide a reference fixed relative to the anatomy of patient P and to any two or three-dimensional models of the patient anatomy generated by the images. In other embodiments, alternative fiducial elements on fiduciary apparatus 360, such as features like sensor holder 372, the reference portion 351 of shape sensor fiber 353 positioned in sensor holder 372, or even fiduciary apparatus 360 itself can be imaged to establish the fixed patient reference.

Before initiating the interventional procedure, the reference portion 351 of the shape sensor fiber 353 is placed in the sensor holder 372 with the connector 374 connected to the connector 382. The reference portion 351 is thus held fixed in the predefined configuration of the sensor holder 372 relative to the fiduciary apparatus 360. Thus connected, the reference portion 351 of the shape sensor fiber 353 provides a known orientation of the proximal end of the shape sensor fiber relative to the fiduciary apparatus 360. The interrogation system 376 interrogates the shape sensor fiber 353 to determine the pose of the distal tip and the shape of the flexible catheter body 354. This sensed relative pose and shape data for the catheter body 354 is known relative to the fiber reference portion 351, which is registered to the fiduciary apparatus 360. Thus, processing the relative pose and shape information for the catheter body 354 with the registration information for the reference portion 351 of the shape sensor fiber provides the pose and shape of the catheter body 354 relative to the patient P.

Figure 7:
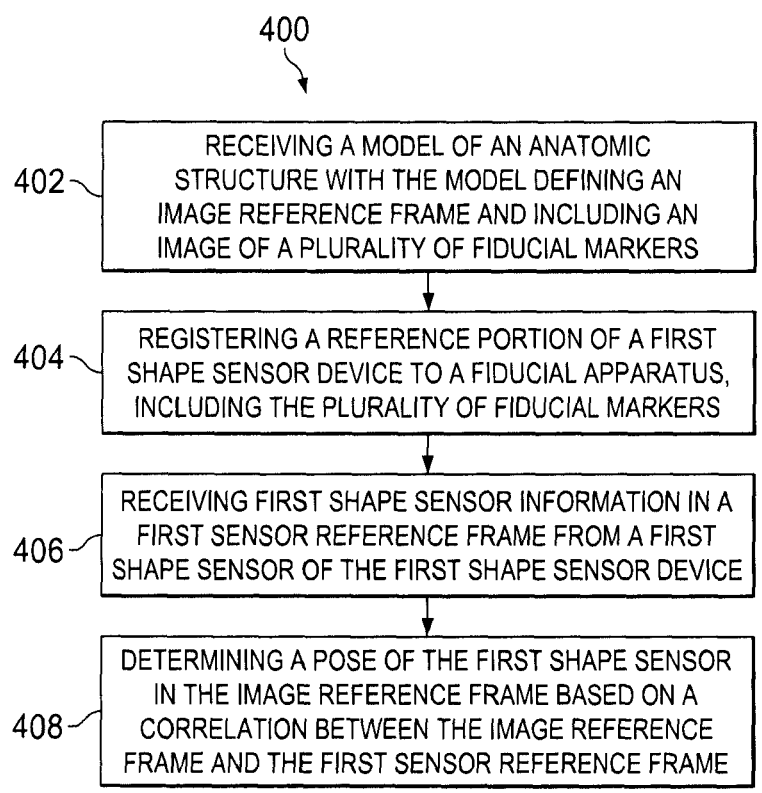
FIG. 7 illustrates a method of use for an interventional instrument tracking system according to another embodiment of the present disclosure.

FIG. 7 illustrates a method 400 for using the interventional instrument tracking system 350. At 402, a processing system receives a model of an anatomic structure of patient P. The model is generated from images of the patient P taken with the fiduciary apparatus 360 attached. The model defines an image reference frame. The fiducial markings 366 are visible in the model. At 404, the reference portion 351 is coupled to the fiduciary apparatus 360. The reference portion 351 of the shape sensor fiber 353 is thus retained in a predefined configuration relative to the fiducial apparatus 360. In this way, the reference portion 351 is registered to the fiducial apparatus 360. At 406, the shape sensor information is received (in the reference frame of the shape sensor fiber 353) for processing. At 408, the pose of the distal end (or any other portion) of the shape sensor fiber 353 is determined in the image reference frame based on a correlation between the image reference frame and the reference frame of the shape sensor 353. Optionally, an image from the image reference frame that corresponds to the pose of the distal end of the flexible body 354 is displayed. The image may be of the distal end of the flexible body 354 superimposed on an image from the patient model. In some embodiments, the patient model may be updated based on the shape sensor information (e.g., by fitting the patient model to the pose of flexible body 254). Alternatively, the image may be a view from inside the patient model corresponding to the view from the distal end of the flexible body.

Figure 8:
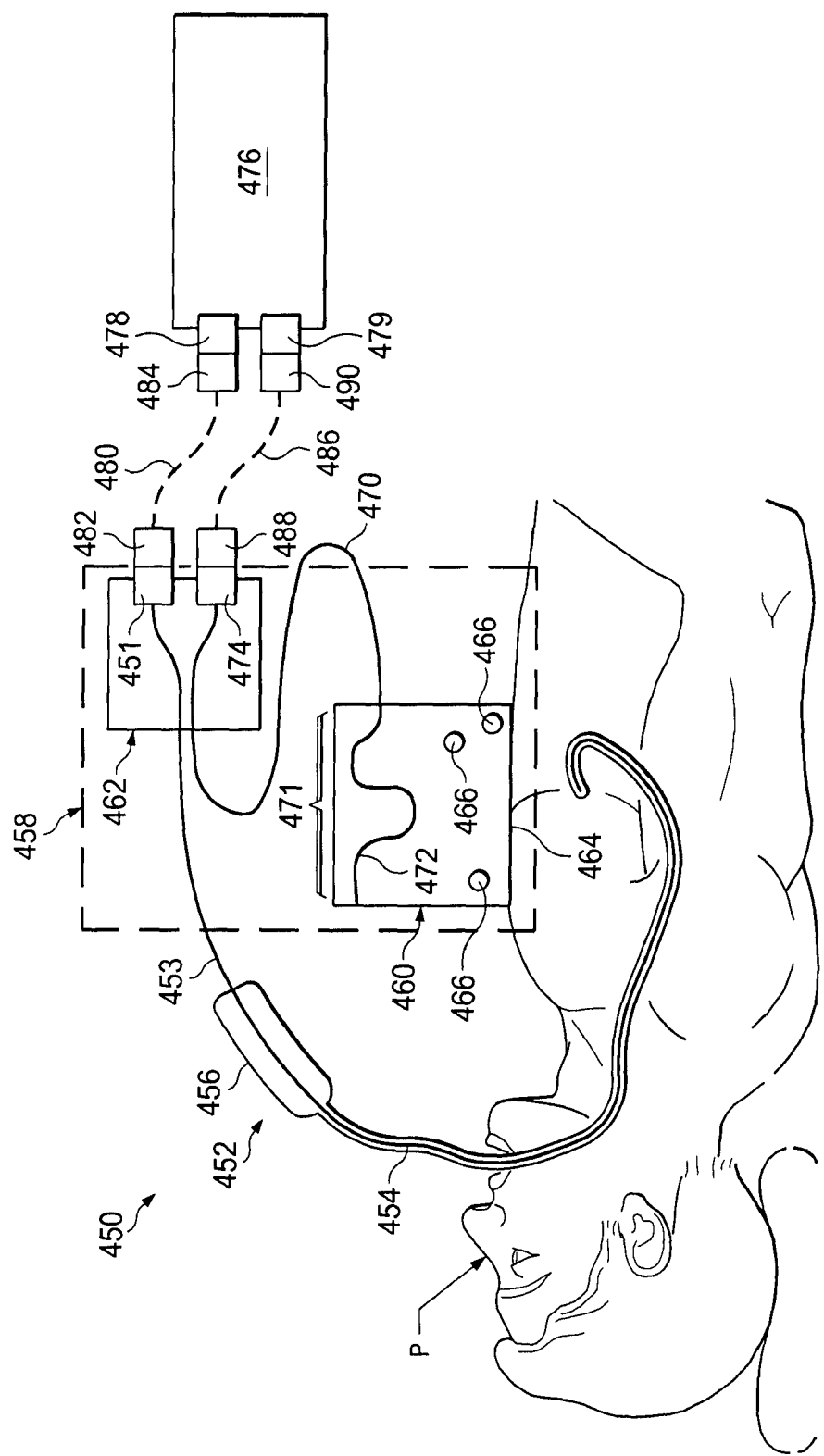
FIG. 8 illustrates an interventional instrument system with a tracking system according to another embodiment of the present disclosure.

FIG. 8 illustrates an interventional instrument tracking system 450 according to embodiments of the present disclosure. The tracking system 450 includes an interventional instrument 452 with a flexible catheter body 454 and an instrument body 456. An optical fiber shape sensor 453 extends within the interventional instrument 452. A proximal end of the shape sensor 453 terminates with a sensor connection component 451. The tracking system 450 also includes a sensor device 458. The sensor device 458 includes a fiduciary apparatus 460 and a reference fixture 462. The fiduciary apparatus 460 includes a surface 464 that is removably attached to the patient P using an adhesive or other chemical or mechanical fixation mechanism. In some embodiments, the fiduciary apparatus 460 can include at least one fiducial marking 466 visible with imaging technology such as fluoroscopy or CT. In various other embodiments, the fiduciary apparatus 360 can include physical features that can be used as fiducials, or can even itself be a fiducial.

An optical fiber shape sensor 470 extends from the fiduciary apparatus 460. The fiduciary apparatus 460 includes a sensor holder 472 that serves as a docking feature configured to mate with and hold a reference portion 471 of the shape sensor fiber 470 in a predefined reference shape. In this embodiment, the sensor holder 472 is a continuous winding channel that receives the shape sensor fiber 470 and maintains the reference portion 471 of the fiber in a predefined shape configuration relative to the fiduciary apparatus 460. The proximal end of the sensor fiber 470 terminates with a sensor connection component 474. In this embodiment, the reference portion 471 of the fiber 470 may serve as the fiducial marking as it is fixed with respect to the fiduciary apparatus and may be visible with the imaging technology.

In various alternative embodiments, the shape sensor 470 may be omitted or supplemented by other components for measuring the relative pose between the fiduciary apparatus 460 and the reference fixture 462. Any of a variety of sensor-based tracking systems may be used to track the relative pose of the reference fixture 462 to the fiduciary apparatus 460. Such tracking systems may include capacitive sensors, piezo-electric sensors, or optical sensors.

The tracking system 450 further includes an interrogation system 476 for generating and detecting the light used to determine the current shapes of the shape sensor fiber 453 and the shape sensor fiber 470. The interrogation system 476 may also process the returned data for display to the clinician. The interrogation system 476 includes connector 478, 479. A fiber link 480 extends between connectors 482, 484. A fiber link 486 extends between connectors 488, 490. In this embodiment, the optical fiber of the fiber links 480, 486 are unsensed (i.e., the shape of the fiber link is not interrogated) and serves to convey optical information between the sensed shape sensors 453, 470 and the interrogation system 476.

In use, the fiduciary apparatus 460 is attached to the patient P. Pre-operative or intra-operative imaging of the patient P is conducted with the fiduciary apparatus 460 attached to the patient anatomy. In this embodiment, the shape sensor fiber 470 may be attached to the fiduciary apparatus 460 during imaging. If present, the fiducial markers 466 are visible in the image and thus provide a reference fixed relative to the anatomy of patient P and to any two or three-dimensional models of the patient anatomy generated by the images. In other embodiments, alternative fiducial elements on fiduciary apparatus 460, such as features like sensor holder 472, the reference portion 471 of shape sensor fiber 470 positioned in sensor holder 472, or even fiduciary apparatus 460 itself can be imaged to establish the fixed patient reference.

Before initiating the interventional procedure, the proximal end of the sensor fiber 470 and the attached connector 474 are coupled to the reference fixture 462. The proximal end of the sensor fiber 453 and the attached connector 451 are also coupled to the reference fixture 462. The reference fixture holds the proximal ends of the sensor fibers 470, 451 in fixed positions and orientations relative to each other and to the reference fixture. The connector 482 of the fiber link 480 is connected to the connector 451 and the connector 484 is connected to the connector 478 of the interrogation system 476. The connector 488 of the fiber link 486 is connected to the connector 474 and the connector 490 is connected to the connector 479 of the interrogation system 476. The interrogation system 476 interrogates the shape sensor fiber 453 to determine the pose of the distal tip and the shape of the flexible catheter body 454. The interrogation system 476 also interrogates the shape sensor fiber 470 to determine the pose of the reference portion 471 of the shape sensor fiber 470. The sensed relative pose and shape data for the catheter body 454 is known relative to the reference fixture 451, and the relative pose and shape data for the reference portion 471 is known relative to the reference fixture 462. Because the connectors 451, 474 are fixed relative to each other and with respect to the reference fixture 462, the reference fixture provides a fixed registration between the shape sensor fibers 453, 470. Thus, processing the relative pose and shape information for the catheter body 454 with the registration information for the reference portion 471 of the shape sensor fiber 470 provides the pose and shape of the catheter body 454 relative to the patient P.

Figure 9:
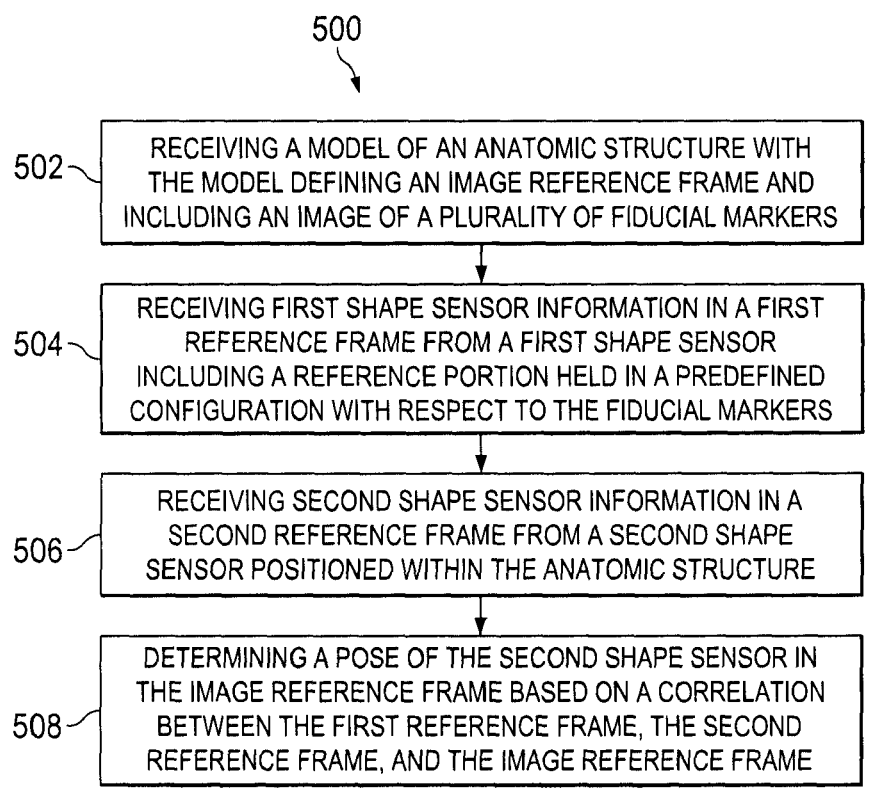
FIG. 9 illustrates a method of use for an interventional instrument tracking system according to another embodiment of the present disclosure.

FIG. 9 illustrates a method 500 for using the interventional instrument tracking system 450. At 502, a processing system receives a model of an anatomic structure of patient P. The model is generated from images of the patient P taken with the fiduciary apparatus 460 attached. The model defines an image reference frame. The fiducial markings 466 are visible in the model. The shape sensor fiber 453 is coupled to the reference fixture 462, and the shape sensor fiber 470 is coupled to the reference fixture 462. At 504, shape sensor information is received from shape sensor fiber 470 (in the reference frame of the shape sensor fiber 470) for processing. At 506, shape sensor information is received from shape sensor fiber 453 (in the reference frame of the shape sensor 453 fiber) for processing. At 508, the pose of the distal end of the shape sensor fiber 353 is determined in the image reference frame based on a correlation between the image reference frame, the reference frame of the shape sensor 353, and the reference frame of the shape sensor 470. Optionally, an image from the image reference frame that corresponds to the pose of the distal end of the flexible body 454 is displayed. The image may be of the distal end of the flexible body 454 superimposed on an image from the patient model. Alternatively, the image may be a view from inside the patient model corresponding to the view from the distal end of the flexible body.

FIG. 10 illustrates an interventional instrument tracking system 550 according to embodiments of the present disclosure. The tracking system 550 includes an interventional instrument 552 with a flexible catheter body 554 and an instrument body 556. An optical fiber shape sensor 553 is separate from and sized for insertion into the interventional instrument 552. The tracking system 550 also includes a sensor device 558. The sensor device 558 includes a fiduciary apparatus 560 and a reference body 562. The fiduciary apparatus 560 includes a surface 564 that is removably attached to the patient P using an adhesive or other chemical or mechanical fixation mechanism. The fiduciary apparatus 560 includes at least one fiducial marking 566 visible with imaging technology such as fluoroscopy or CT. The fiduciary apparatus 560 further includes a sensor docking feature 568 configured to mate with a mating portion 570 of the reference body 562. The sensor docking feature 568 may include one or more recesses, protrusions, mechanical fasteners, adhesive fasteners, magnetic fasteners, or other components for removably connecting the fiduciary apparatus 560 to the reference body 562. When connected, the sensor docking feature 568 and the mating portion 570 maintain the fiduciary apparatus 560 and the reference body 562 in a fixed, predefined spatial relationship.

The reference body 562 include a sensor holder 572 configured to hold a reference portion 551 of the shape sensor fiber 553 in a predefined reference shape. In this embodiment, the sensor holder 572 is a continuous winding channel that receives the shape sensor fiber 553 and maintains the fiber in a predefined shape configuration relative to the reference body 562. In alternative embodiments, the sensor holder may be a series of discrete attachment points to which the sensor fiber may be attached to maintain a known, predefined shape with respect to the reference body. The reference body 562 further includes a sensor connection component 574 in which the sensor fiber 553 terminates for connection to other components of the tracking system 550. The various alternative embodiments, the known configuration may be measurably variable as previously described.

The tracking system 550 further includes an interrogation system 576 for generating, and detecting the light used to determine the current shape of the shape sensor fiber 553. The interrogation system 576 may also process the returned data for display to the clinician. The interrogation system 576 includes a connector 578. A fiber link 580 extends between connectors 582, 584. In this embodiment, the optical fiber of the fiber link 580 is unsensed (i.e., the shape of the fiber link is not interrogated) and serves to convey the optical information from the sensed shape sensor 553 to the interrogation system 576. In use, the connector 582 of the fiber link 580 is connected to the connector 574 and the connector 584 is connected to the connector 578.

In use, the fiduciary apparatus 560 is attached to the patient P. Pre-operative or intra-operative imaging of the patient P is conducted with the fiduciary apparatus 560 attached. The fiducial markers 566 are visible in the image and thus provide a reference fixed relative to the anatomy of patient P and to any two or three-dimensional models of the patient anatomy generated by the images. Before initiating the interventional procedure, the sensor fiber 553 is inserted into the flexible catheter body 554. The reference body 562 is coupled to the fiduciary apparatus 560 and is held in a predefined configuration relative to the fiduciary apparatus by the docking feature 568 and the mating portion 570. Thus connected, the reference portion 551 of the shape sensor fiber 553 provides a known orientation of the proximal end of the shape sensor fiber relative to the fiduciary apparatus 560. The interrogation system 576 interrogates the shape sensor fiber 553 to determine the pose of the distal tip and the shape of the flexible catheter body 554. This sensed relative pose and shape data for the catheter body 554 is known relative to the reference portion 551 of the shape sensor fiber, which is registered to the fiduciary apparatus 560. Thus, processing the relative pose and shape information for the catheter body 554 with the registration information for the reference portion 551 of the shape sensor fiber provides the pose and shape of the catheter body 554 relative to the patient P. Further details of the method processing information from the sensor fiber 553 are similar to those described for FIG. 5.

In this embodiment, the sensor fiber 553 is separable from the flexible catheter body and thus, the sensor fiber 553 may be used with other types of instruments including bronchoscopes or other devices that include a lumen sized to receive the fiber 553.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical tracking system comprising:
   a fiducial apparatus body including
   a sensor docking feature formed in the fiducial apparatus body and configured to mate with a mating portion of a reference body that retains a reference portion of a sensor device in a known shape configuration;
   at least one imageable fiducial marker; and
   a surface of the fiducial apparatus body configured for attachment to an anatomy of a patient, wherein
   the reference body, including the mating portion, includes a sensor connection component for interfacing the sensor device with a sensor interrogation system, the sensor device including a first shape sensor, the reference portion of the sensor device being a portion of the first shape sensor that passes through the reference body.

2. The medical tracking system of claim 1 further comprising an elongated flexible instrument in which a distal portion of the first shape sensor extends.

3. The medical tracking system of claim 2 wherein the first shape sensor is fixedly coupled to the elongated flexible instrument.

4. The medical tracking system of claim 1 further comprising the sensor interrogation system including a processor configured to receive information from the first shape sensor.

5. The medical tracking system of claim 4 further comprising an optical fiber link configured to connect the sensor interrogation system and the first shape sensor and convey information from the first shape sensor to the sensor interrogation system, the reference body having a sensor connector configured to mate with a distal connector of the optical fiber link.

6. The medical tracking system of claim 1 wherein the first shape sensor includes an optical fiber shape sensor.

7. The medical tracking system of claim 1 further comprising a reference fixture including a first sensor connector configured to hold a proximal end of the first shape sensor in a fixed pose.

8. The medical tracking system of claim 7 wherein the reference fixture further includes a second sensor connector configured to hold a proximal end of a second shape sensor in a fixed pose, wherein the reference fixture retains the proximal ends of the first and second shape sensors in a fixed relationship to each other.

9. The medical tracking system of claim 8 further comprising an elongated flexible instrument in which a distal end of the second shape sensor extends.

10. The medical tracking system of claim 1 wherein the known shape configuration is a fixed, predefined configuration.

11. The medical tracking system of claim 10 wherein the sensor docking feature includes a winding channel configured to receive and retain the reference portion of the sensor device in the predefined configuration.

12. The medical tracking system of claim 10 wherein the sensor docking feature includes a plurality of recessed features configured to receive a plurality of projections of the mating portion to retain the fiducial apparatus body and the reference body in a predefined spatial relationship.

13. The medical tracking system of claim 10 wherein the sensor docking feature includes a plurality of projections configured for receipt in a plurality of recesses of the mating portion to retain the fiducial apparatus body and the reference body in a predefined spatial relationship.

14. The medical tracking system of claim 1 wherein the known shape configuration is a measurably variable configuration.

15. The medical tracking system of claim 14 wherein the measurably variable configuration is an insertion distance.

16. The medical tracking system of claim 14 further including a variation tracking system for measuring a pose variation between the reference body and the fiducial apparatus body.

17. A method for medical instrument tracking, the method comprising:
   receiving a model of an anatomic structure, the model defining an image reference frame and including an image of a fiducial apparatus including at least one fiducial marker;
   registering a reference portion of a first shape sensor device to the at least one fiducial marker when the fiducial apparatus including the at least one fiducial marker is coupled to the first shape sensor device, by a mating feature and a docking feature, such that the reference portion of the first shape sensor device passes through a reference body such that the reference portion is retained by the reference body in a known shape configuration relative to the at least one fiducial marker;
   receiving first shape sensor information in a first sensor reference frame from a first shape sensor of the first shape sensor device; and
   determining a pose of the first shape sensor in the image reference frame based on a correlation between the image reference frame and the first sensor reference frame to register the first shape sensor device to the model.

18. The method of claim 17 further comprising displaying an image from the image reference frame that corresponds to the pose of the first shape sensor.

19. The method of claim 17 wherein receiving the model of the anatomic structure includes receiving a model derived from a set of three dimensional volumetric images.

20. The method of claim 17 wherein receiving first shape sensor information includes receiving information generated from an optical fiber shape sensor.

21. The method of claim 17 wherein receiving first shape sensor information includes receiving the first shape sensor information from the first shape sensor coupled to an elongated flexible instrument extending with the anatomic structure.

22. A method for medical instrument tracking, the method comprising:
receiving a model of an anatomic structure, the model defining an image reference frame and including a model of at least one fiducial marker;
receiving first shape sensor information in a first reference frame from a first shape sensor including a reference portion that passes through a reference body such that the reference portion is retained by the reference body in a known shape configuration with respect to the at least one fiducial marker, the reference portion being included in the first shape sensor;
receiving second shape sensor information in a second reference frame from a second shape sensor positioned within the anatomic structure; and
determining a pose of the second shape sensor in the image reference frame based on a correlation between the first reference frame, the second reference frame, and the image reference frame, wherein
the first shape sensor includes a sensor connection component for interfacing the first shape sensor with a sensor interrogation system.

23. The method of claim 22 further comprising displaying an image from the image reference frame that corresponds to the pose of the second shape sensor.

24. The method of claim 22 wherein receiving the model of the anatomic structure includes receiving a model from a set of three dimensional volumetric images.

25. The method of claim 22 wherein receiving first shape sensor information includes receiving information generated from an optical fiber shape sensor.

26. The method of claim 22 wherein receiving second shape sensor information includes receiving information generated from an optical fiber shape sensor.

27. The method of claim 22 wherein receiving second shape sensor information includes receiving the second shape sensor information from the second shape sensor coupled to an elongated flexible instrument extending with the anatomic structure.

28. A system comprising:
a memory for storing a model data set representing an anatomic structure, the model data set having a plurality of model data points for the anatomic structure with a known relation to one or more fiducial markers, and for storing received shape data from an optical fiber sensor in an instrument interacting with the anatomic structure; and
a processor configured to:
receive the model data set representing the anatomic structure, the model defining an image reference frame and including an image of at least one fiducial marker;
register a reference portion of a first shape sensor device to the at least one fiducial marker when a fiducial apparatus including the at least one fiducial marker is coupled to the first shape sensor device such that the reference portion of the first shape sensor device passes through a reference body such that the reference portion is retained by the reference body in a known shape configuration relative to the at least one fiducial marker;
receive first shape sensor data in a first sensor reference frame from a first shape sensor of the first shape sensor device, the first shape sensor data including shape sensor data from the reference portion of the first shape sensor device; and
determine a pose of the first shape sensor in the image reference frame based on a correlation between the image reference frame and the first sensor reference frame.

29. The system of claim 28, wherein the processor is further configured to update the model data set based on the shape data.

30. The system of claim 29, wherein the processor is configured to update the model data set based on the pose of the first shape sensor using the shape data, and fitting the model data set to the pose.

31. The system of claim 28, wherein the processor is further configured to generate an image data set comprising model image data generated from the model data set and instrument image data generated from the shape data, wherein the instrument image data is registered with the model image data.

32. The system of claim 31, further comprising a display for receiving the image data set and showing the instrument image data superimposed on the model image data.

33. A medical system comprising:
a fiducial apparatus for attachment to a patient; and
a coupling for holding a first portion of a fiber optic shape sensor in a predetermined shape configuration relative to the fiducial apparatus wherein the coupling includes a reference body having a winding channel configured to receive and retain the first portion of the fiber optic shape sensor in the predetermined shape configuration, the coupling including a sensor connection component for interfacing the fiber optic shape sensor with a sensor interrogation system, wherein
the first portion of the fiber optic shape sensor passes through the reference body including the winding channel.

34. The medical system of claim 33, wherein the fiducial apparatus comprises at least one of a fiducial marker and a fiducial feature visible by a medical imaging system.

35. The medical system of claim 33, wherein the reference body is configured to removably mate with the fiducial apparatus.

36. The medical system of claim 33, wherein the coupling comprises one or more features of the fiducial apparatus for maintaining the fiber optic shape sensor in the predetermined shape configuration.

37. The medical system of claim 33, further comprising an instrument for interacting with an anatomical structure of the patient,
wherein a second portion of the fiber optic shape sensor is coupled to the instrument.

38. The medical system of claim 37, further comprising a processor configured to receive a model of the anatomical structure registered to the fiducial apparatus, receive shape sensor data from the second portion of the fiber optic shape sensor registered to the fiducial apparatus, and register the instrument to the anatomical structure based on the model and the shape sensor data.

\* \* \* \* \*